(12) United States Patent
Gueret

(10) Patent No.: US 6,723,306 B2
(45) Date of Patent: Apr. 20, 2004

(54) ARTICLE FOR APPLYING ARTIFICIAL TANNING AGENT AND METHOD OF MAKING

(75) Inventor: Jean-Louis Gueret, Paris (FR)

(73) Assignee: L'Oreal, Paris (FR)

( * ) Notice: Subject to any disclaimer, the term of this patent is extended or adjusted under 35 U.S.C. 154(b) by 64 days.

(21) Appl. No.: 10/161,877

(22) Filed: Jun. 5, 2002

(65) Prior Publication Data

US 2002/0192270 A1 Dec. 19, 2002

(30) Foreign Application Priority Data

Jun. 5, 2001 (FR) ............................................. 01 07309

(51) Int. Cl.⁷ ............................ A61K 7/42; A61K 7/00; A61K 9/14; A61K 9/70
(52) U.S. Cl. .................... 424/59; 424/400; 424/401; 424/484; 424/449
(58) Field of Search ........................... 424/59, 60, 400, 424/401, 484, 449

(56) References Cited

U.S. PATENT DOCUMENTS

| | | | |
|---|---|---|---|
| 5,078,160 A | 1/1992 | Carbonnier | 132/320 |
| 5,968,533 A | 10/1999 | Porter et al. | 424/401 |
| 5,972,360 A | 10/1999 | Braun | 424/401 |
| 6,063,398 A | 5/2000 | Gueret | 424/443 |

FOREIGN PATENT DOCUMENTS

| | | |
|---|---|---|
| EP | 0 953 460 | 11/1999 |
| EP | 0 998 903 | 5/2000 |
| WO | WO 98/18441 | 5/1998 |
| WO | WO 99/13861 | 3/1999 |
| WO | WO 99/21532 | 5/1999 |
| WO | WO 00/16752 | 3/2000 |
| WO | WO 01/08658 | 2/2001 |

*Primary Examiner*—Shelley A. Dodson
(74) *Attorney, Agent, or Firm*—Oblon, Spivak, McClelland, Maier & Neustadt, P.C.

(57) ABSTRACT

An article for applying a skin care product, particularly an artificial tanning agent to the skin. The article includes an adhesive matrix disposed between at least two layers that are permanently bonded to the matrix, with at least one of the layers being permeable to a liquid. The matrix contains at least one artificial tanning agent suitable for acting on the skin when the matrix is put into contact with the liquid so that the artificial tanning agent can be applied to the skin after contacting the article with the liquid. A method of making the article is also provided.

68 Claims, 2 Drawing Sheets

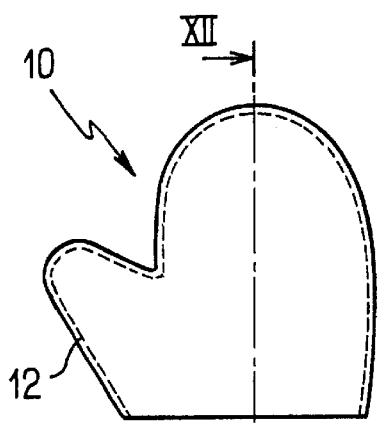
FIG_1
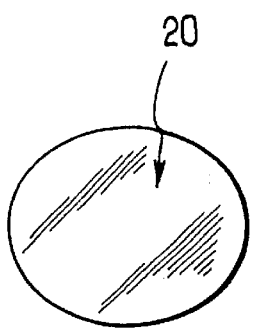
FIG_2
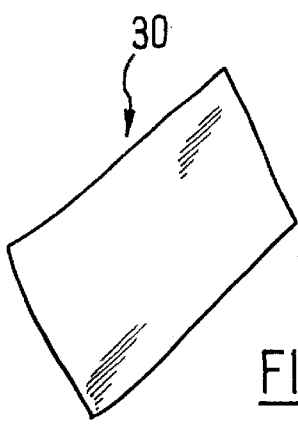
FIG_3
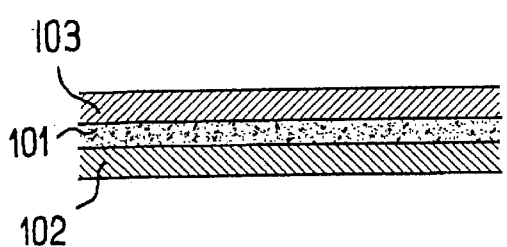
FIG_4
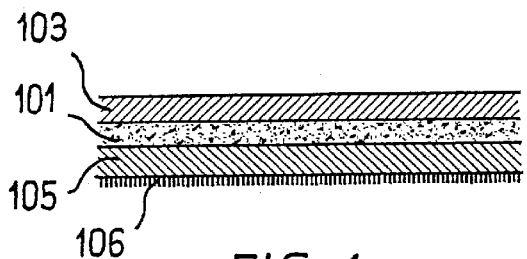
FIG_6
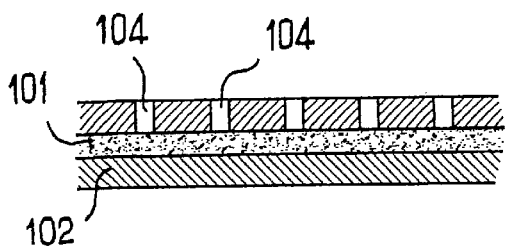
FIG_5
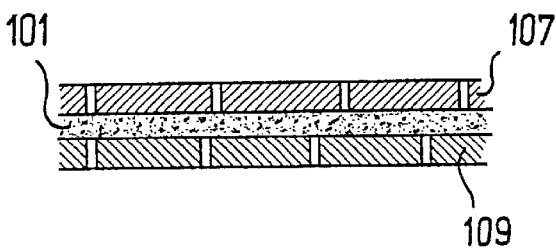
FIG_7

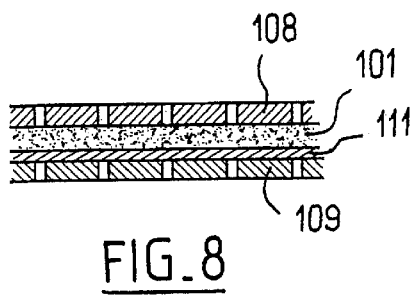
FIG_8
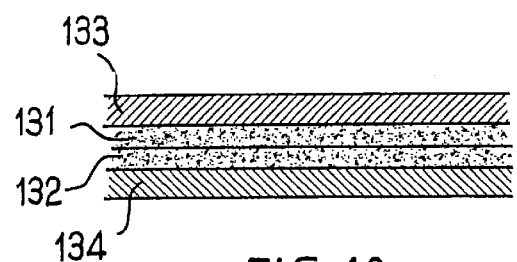
FIG_10
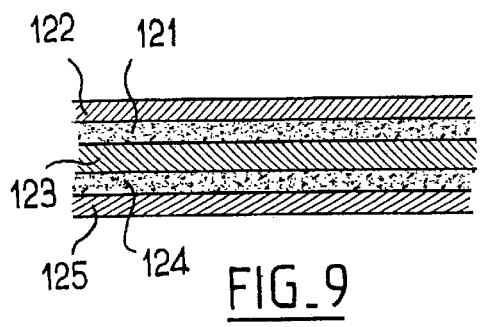
FIG_9
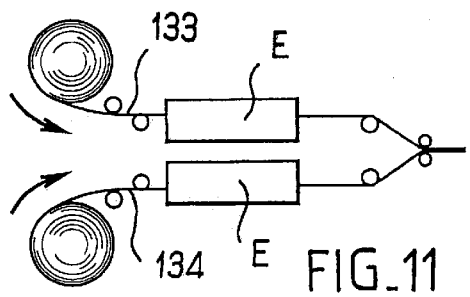
FIG_11
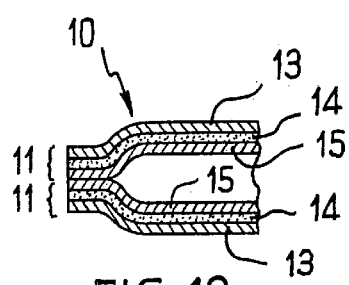
FIG_12
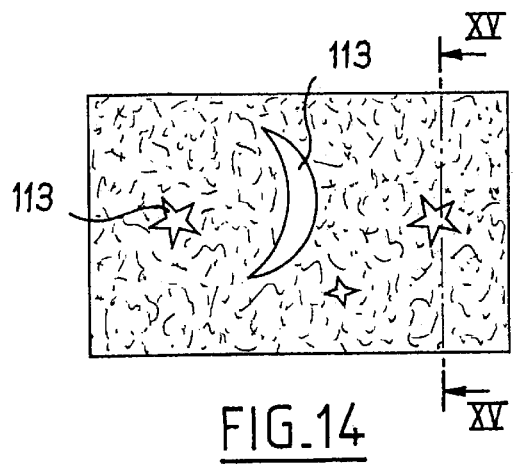
FIG_13
FIG_14
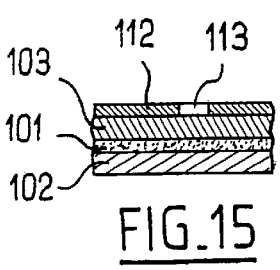
FIG_15
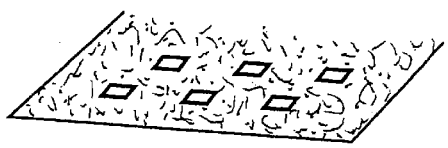
FIG_16

ARTICLE FOR APPLYING ARTIFICIAL TANNING AGENT AND METHOD OF MAKING

CROSS REFERENCE TO RELATED APPLICATIONS

This document claims priority to French application number 0107309 filed Jun. 5, 2001, the entire content of which is hereby incorporated by reference.

FIELD OF THE INVENTION

The present invention relates to artificial tanning agents, and particularly to an article for applying artificial tanning agents, and a method for making such an article.

BACKGROUND OF THE INVENTION

Discussion of Background

Artificial tanning creams can be packaged in pots or tubes and applied to the body or the face using the fingers. However, it is difficult to uniformly apply the cream with this approach, and there is a risk of non-uniform coloring the skin. In addition, the fingers used for spreading the cream can also be marked or discolored. In addition, in order to preserve the tanning agent, the cream contains preservatives that can lead to irritation of the skin.

U.S. Pat. No. 5,972,360 discloses a towelette impregnated with an artificial tanning agent. Such a towelette makes it easier to apply the desired quantity of the agent on the skin, but the user nevertheless runs the risk of discoloring the fingers that come into contact with the towelette. In addition, in order to ensure that the agent is properly conserved, the towelette must be packaged in a bag that is leaktight and opaque, and thus relatively expensive. Since the towelette is not dry, preservatives are also likely to be used.

International patent application No. WO 01/08658 discloses a cleaning cloth that is impregnated with a surfactant. The cloth includes two layers, e.g., constituted by non-woven fabrics. The cloth can also contain an artificial tanning agent placed on one of the layers and then covered by the other layer. One of the layers can be impregnated with the artificial tanning agent, in particular by spraying. However, difficulties can be encountered with the agent impregnating one of the layers throughout its thickness. In addition, the manufacture of such pieces of cloth can be relatively complex.

European patent application No. EP 0 998 903 (which has a pending U.S. counterpart Ser. No. 09/418,825 and which is incorporated herein by reference) discloses a patch comprising both a matrix capable of containing an artificial tanning agent and a permeable support. The artificial tanning agent forms a solution when the matrix is brought into contact with a suitable liquid. The matrix is covered on one face by a removable protective film. Applying an artificial tanning agent by means of a patch stuck to the skin is not always satisfactory, since there is always a risk of the skin being colored in non-uniform manner as a result of the length of time the patch remains stationary on the skin.

SUMMARY OF THE INVENTION

There exists a need for a device or article that allows an artificial tanning agent to be easily applied to the skin, while allowing the agent to be conserved properly, and also reducing the risk of the user discoloring the fingers. There is also a need to be able to obtain non-uniform coloring of the treated surface, should that be desired, e.g., in order to decorate it with a design or motif.

The invention provides a novel applicator device and method in which an adhesive matrix is disposed between at least two layers that are permanently bonded to the matrix, with at least one of the layers being permeable to a liquid. The matrix contains at least one artificial tanning agent suitable for acting on the skin when the matrix is put into contact with a liquid, which can be, for example, water or a liquid that includes water and alcohol.

As used herein, two or more structural elements that are "permanently bonded" to each other cannot be readily or easily separated from one another through the use of a completely manually-applied pulling force. For example, a release layer in contact with an adhesive on a bandage would not be "permanently bonded" to the remainder of the bandage.

The term "artificial tanning agent" is used in the present invention to encompass compounds which serve themselves to color the skin, i.e. self-tanning or sunless tanning agents such as dihydroxyacetone (DHA) or erytrulose, for example, as well as agents which require exposure to ultraviolet (UV) radiation, i.e., tanning accelerators such as melanin precursors, for example. The artificial tanning agent can optionally be tinted.

The invention enables the artificial tanning agent to be conserved properly without using preservatives since it may be stored in a substantially anhydrous medium within the matrix. Manufacture of the device can also be relatively simple since it is the matrix containing the artificial tanning agent which provides the fastening or adhesion between the layers.

In addition, the article can be made in such a manner as to be non-adhesive or non-stick with respect to the surface to which the tanning agent is to be applied, so as to be easily moved in contact with the skin during application, thus making it possible to obtain color that is uniform. Alternately, where desired, the article can be made to have a certain outline or profile, and the permeable layer facing the skin can be made in such a manner as to allow the matrix, once the device has been impregnated with the liquid, to burst or break-up and pass through the permeable layer. The matrix then causes the outside face of the layer to become permeable to the adhesive, thus enabling it to be held stationary on the skin for a length of time that is sufficient to mark the skin with a desired design or motif by changing the color of the skin. In a variant, or where appropriate, selected portions of the permeable layer can also be made to be impermeable to the artificial tanning agent e.g., by covering the permeable layer with an impermeable web that is perforated in certain locations, or by selectively printing, such as by silkscreen printing, on the permeable layer using a substance that impedes or prevents the artificial tanning agent from diffusing towards the skin. Alternatively selected portions of the layer can be treated in a manner that accelerates (e.g., by a mechanical and/or chemical treatment that increases the porosity or permeability of the substrate) such diffusion so that the tanning agent is better delivered to the areas where a design is desired. The motif made on the skin may be constituted, for example, by a representation of the moon, a star, or any other shape or design.

In one embodiment, the matrix contains one or more compounds soluble in the liquid used in sufficient quantity such that the matrix at least partially loses its cohesion on making contact with the liquid. This arrangement can facilitate delivery of the artificial tanning agent through the permeable layer facing the skin.

In another aspect of an embodiment, the matrix contains a filler of one or more compounds capable of swelling on coming into contact with the liquid in sufficient quantity for the matrix to lose its cohesion on coming into contact with the liquid. As with the above embodiment, this arrangement can facilitate delivery of the artificial tanning agent.

The matrix may also contain one or more moisture absorbing compounds. Where a moisture-absorbing compound is included, the moisture-absorbing compound is preferably 0.2% to 60%, and more preferably 0.5% to 40% by weight of the matrix. By way of example, this compound may be selected from the following list: polyacrylates; silica; cotton fibers; starches; alginates; calcium carbonates; magnesium carbonates; viscose; cellulose; and lyophilisates.

The matrix may also contain a filler of one or more substantially inert compounds, such as a polyamide powder or microbeads, for example, in order to encourage bursting or breaking-up of the matrix on coming into contact with the liquid.

In accordance with the invention, when a liquid (e.g., water or a water and alcohol solution) is applied to the article, it wets the matrix and allows the tanning agent to be delivered to the skin through one or more of the layers that are permeable to the tanning agent. The tanning agent can be delivered by being dissolved by the liquid and/or by being carried as a suspension in the liquid. Depending upon the proportions of the tanning agent with respect to the remainder of the matrix, it can also be desirable to at least partially degrade the remainder of the matrix to increase the proportion of the tanning agent contained within the matrix that can be exposed to the liquid. As discussed above, the degradation of the matrix can be accomplished by including (in addition to the adhesive that holds the substrate layers together and the tanning agent) one or more materials or compounds that are: dissolved by the liquid; absorb the liquid or swell when contacted by the liquid to encourage breaking-up or bursting of the matrix; or a substance that becomes suspended/washed away or otherwise loses its structural integrity when exposed to the liquid to assist in breaking up of the matrix and expose the tanning agent to the liquid. Preferably, the adhesive is present in sufficient quantities such that adhesion of the substrate layers to the matrix (and thus to each other) is maintained after the matrix is contacted with the liquid. Where it is desired to provide a sticky or adhesive surface to the article upon wetting with a liquid (to hold the article temporarily against the skin, e.g., to apply a design or motif to the skin), a second adhesive or filler can be provided in the matrix (i.e., other than the adhesive which holds the layer to the matrix), with the second adhesive or filler activated or dissolved upon contact with the liquid so that it can pass through one of the permeable layers and assist in temporarily holding the article against the skin to apply the design. This second adhesive or filler provides a sticky or tacky temporary adhesion of the article to the skin so that the user can remove the article when desired. The tanning agent could be present within the matrix as a liquid, gel or cream (within pockets or encapsulated portions defined by the matrix) which is released as the matrix is wetted with the liquid and the matrix degrades or partially breaks-up. However, the artificial tanning agent is preferably present in solid, dry form (until use is desired) for ease of manufacture and to minimize the need for preservatives.

In addition to the artificial tanning agent, the matrix can contain one or more active agents selected from the following list: vitamin C; vitamin A; vitamin F; glycerin; laponite; wetting agents; collagen; salicylic acid; do acid; caffeine; essential aromatic oils; coloring agents; anti-oxidants; free radical scavengers; moisturizers; depigmenting agents; liporegulators; antiacne agents; antidandruff agents; anti-aging agents; softeners; antiwrinkle agents; keratolitic agents; anti-inflammatory agents; fresheners; healing agents; vascular protectors; antibacterial agents; antifungal agents; antiperspirants; deodorants; skin conditioners; anesthetics; immunomodulators; nourishing agents; melatonin; and dehydroepiandrosterone (DHEA).

The matrix may also include magnetizable or magnetized particles.

The adhesive matrix may be based on an adhesive that is not soluble in water when in the cross-linked state. Examples of adhesives that can be used in the adhesive matrix include: vinyl-based adhesives; polyvinyl alcohol (PVA)-based adhesives; polyvinyl pyrrolidene (PVP)-based adhesives; pseudolatex-based adhesives; acrylic polymer-based adhesives; polyurethane-based adhesives; and latex elastomer-based adhesives. The adhesive should be selected to be compatible with the artificial tanning agent and the active agent(s) used (if any).

Examples of preferred substrate layers that can be used with the matrix include: a non-woven fabric, preferably an aerated non-woven fabric that optionally can be perforated; a foam; a woven fabric; plastics (that optionally can be perforated), and a metallized film (that can also optionally be perforated). By way of example, a non-woven fabric can be an aerated and perforated so as to enable the matrix, after coming into contact with the liquid, to pass through the perforations in the non-woven fabric and between the fibers away from the perforations, where appropriate, after it has burst, thereby facilitating transfer of the artificial tanning agent to the skin, and possibly conferring adhesive properties to the outside surface of the article.

In one embodiment, the matrix is located between a layer that is permeable and a layer that is impermeable to the liquid. In particular, the matrix can be located between a hydrophilic layer and a layer that is impermeable to the liquid, e.g., between a hydrophilic non-woven fabric and an impermeable plastic film. The leakproof plastic film may itself be covered in a non-woven fabric or in flocking. The presence of an impermeable layer is useful for isolating the user's fingers from the matrix at the time of use, thus enabling the user to avoid marking or discoloration of the fingers.

In another particular embodiment, the matrix is located between two layers that are permeable to the liquid. In particular, the matrix can be located between two hydrophilic layers or between a hydrophilic layer and a hydrophobic layer. The matrix may thus be placed between a woven fabric or a non-woven fabric that is hydrophilic and a woven fabric or a non-woven fabric that is hydrophobic. In one example, the matrix can be placed between a perforated plastic film and a hydrophilic nonwoven fabric. The use of a hydrophobic non-woven fabric makes it possible to obtain poor wetting of one surface of the device or article, which is the surface held in the hand, while nevertheless ensuring that the surface is more pleasing to touch than it would be if constituted solely by a leakproof plastic film.

By way of example, the device can be in the form of a disk, as a piece of cloth (having a rectangular, square, or various other shapes), or a glove. When it is in the form of a glove, it preferably includes a layer that is impermeable to the liquid used, with the impermeable layer disposed between the matrix and the inside of the glove.

In accordance with the invention, the layers between which the matrix is located may be free from any artificial tanning agent on their surfaces remote from the matrix (the outer surfaces of the article) until the matrix is contacted with the liquid. This ensures that the artificial tanning agent is relatively well protected from UV radiation, particularly when the layers outside the matrix are adapted to provide a UV radiation barrier. There is therefore no need to provide for individual opaque packaging, and this reduces the cost of the article quite considerably.

Another advantageous aspect of the invention provides a box containing a plurality of articles such as disks, pieces of cloth, or gloves in accordance with the invention.

A further advantageous aspect of the invention provides a kit that includes a device or article as described above together with a receptacle containing the liquid. The liquid can be, for example, water, or a liquid that includes water an alcohol such as a water and alcohol lotion, and optionally contains one or more active agents suitable for encouraging penetration of the artificial tanning agent into the skin.

The article may also be in the form of a roll, optionally with perforations making it easier to tear into smaller sized articles or sheets.

According to an advantageous method for manufacturing the article of the invention, an artificial tanning agent is incorporated in an adhesive-based matrix. The matrix is placed between at least two layers, at least one of which is permeable to a liquid, with the liquid enabling the artificial tanning agent to act on the skin when the matrix is put into contact therewith. The matrix need not be in an aqueous phase during manufacture and/or storage of the article, thus making it possible to avoid using preservatives.

In one example of the method, the matrix is assembled with one of the layers without impregnating it completely through, with the impregnation preferably extending to no more than 25% of its thickness, for example. The other layer, e.g., the layer which is more permeable to the liquid used and through which the artificial tanning agent is released to the skin, may be fixed on the matrix merely by adhesive contact. Prior to contacting the liquid, the matrix is thus kept away from the outside surfaces of the article, thereby enabling the matrix to be protected, in particular from UV radiation.

BRIEF DESCRIPTION OF THE DRAWINGS

The invention will be better understood on reading the following detailed description of non-limiting embodiments and examples of the invention, particularly when read in conjunction with the accompanying drawings in which:

FIGS. 1 to 3 show various examples of applicator devices or articles in accordance with the invention;

FIGS. 4 to 10 show cross-sections of various examples of possible structures according to the invention;

FIG. 11 depicts the manufacture of the structure of FIG. 10;

FIG. 12 is a cross-section on line XII—XII of FIG. 1;

FIG. 13 is a diagram showing a device cut out in such a manner as to enable a motif to be made on the skin;

FIG. 14 shows a variant enabling the skin to be decorated;

FIG. 15 is a cross-section on line XV—XV of FIG. 14; and

FIG. 16 is a diagram of a perforated aerated nonwoven fabric.

DETAILED DESCRIPTION OF THE PREFERRED EMBODIMENTS

Examples of various aspects of the invention will now be described with reference to the drawings. The drawings are intended as illustrative of the invention and are not necessarily to scale. It is to be understood that the dimensions and proportions can be varied.

The applicator device of the invention can have a variety of shapes. In particular, the article can be in the form of a glove 10, as shown in FIG. 1, in the form of a disk 20 as shown in FIG. 2, or in the form of a piece of cloth 30 as shown in FIG. 3. Although the cloth is shown as rectangular in FIG. 3, it is to be understood that the cloth can have various shapes. For the various shapes and forms of the article, a composite structure is utilized as described below with reference to the various non-limiting examples of FIGS. 4 to 10. In general, the composite structure includes an adhesive matrix which contains the artificial tanning agent, and respective layers of a material different from that of the matrix are disposed on either side of the matrix, with at least one of the layers being permeable to a liquid to enable the artificial tanning agent to pass in solution for application to the skin of the user.

The composite structure is preferably in the form of a relatively flexible sheet. It can be used as a single sheet of various shapes, or two or more sheets can be assembled e.g., to form a glove as shown in FIG. 1. Where two or more sheets are assembled, the sheets can be the same or they can have different structures.

In the example of FIG. 4, the composite structure includes an adhesive matrix 101 sandwiched between two layers 102 and 103 that are permeable to the liquid that will be used to assist application of the artificial tanning agent. The adhesive matrix 101 includes a permanent adhesive that is not entirely soluble in the liquid used, serving to provide sufficient attachment of the two layers 102 and 103 even when the structure 100 is wetted by said liquid. The layers 102 and 103 can be constituted, for example, by a textile film, a nonwoven fabric, or a cellular material such as a foam. The composite structure can be made by coating the matrix with its solvent while disposed on a silicone paper, and then in applying a non-woven or other fabric against the matrix. The matrix should be allowed to penetrate to a shallow depth into the non-woven fabric preferably, e.g., to a depth 25% or less. Thereafter, the assembly is heated to evaporate off the solvent, the silicone paper is withdrawn, and the second layer of non-woven fabric is applied to the matrix and is held thereto by adhesive contact. The solvent is utilized for good fluidity or flowability of the adhesive matrix to ease application to the first layer. In a preferred form, the matrix does not rely upon the solvent to enhance bonding of the matrix, and therefore, the second layer bonds to the matrix after the solvent has evaporated. The second layer can be constituted by a perforated non-woven fabric of light weight, for example. The manufacturing method descried above serves to associate such a lightweight perforated non-woven fabric with the matrix without any danger of the matrix impregnating it over an excessive portion of the thickness of the fabric.

In the example of FIG. 5, one of the layers has perforations 104 in order to encourage exchange between the exterior of the article and the matrix 101. The layer which includes these perforations can be made of a permeable material like the layer 103 in the preceding example, or in a variant it can be made of an impermeable material, e.g., a plastic film. The perforations can be directed towards the surface to be treated or otherwise. FIG. 16 represents a perforated aerated non-woven fabric as an illustration. It is to be understood that the size and density/number of the perforations can vary.

FIG. 6 shows a composite structure in which the matrix 101 is placed between a layer 103 that is permeable to the liquid used and a layer 105 that is impermeable to the liquid and can be formed, for example, with a plastic film. In order to make the plastic film more agreeable or pleasant to the touch, it can be coated or covered in flocking 106 or in a web of non-woven fabric.

FIG. 7 illustrates an arrangement in which the matrix is placed between two perforated layers 107 and 109. The material used for making the layers 107 and 109 can be a plastic material, a woven fabric, or a non-woven fabric, for example. As shown in FIG. 8, it is also possible to place a leakproof plastic film 111 between one of the outside layers and the matrix. The layers 108 and 109 preferably are hydrophilic non-woven fabrics, or fabrics in which at least a portion of the fibers are hydrophilic fibers.

In the embodiment of FIG. 9, the composite structure includes a first adhesive matrix 121 sandwiched between layers 122 and 123, and a second adhesive matrix 124 sandwiched between the layer 123 and another layer 125. The layer 123 that is sandwiched between the matrices 121 and 124 can include a material that is permeable to the liquid used, or that is impermeable thereto. When the selected material is impermeable to the liquid, the layers 122 and 125 are permeable to the liquid, thus enabling the liquid to reach the matrices 121 and 124 when the composite structure is wetted. The matrices 121 and 124 can have different active agents, thus enabling the user to treat the skin in different ways depending on whether the layer 122 or the layer 125 is applied to the skin. Only the layer 122 enables the active agents contained in the matrix 121 to diffuse towards the skin, given the existence of the barrier constituted by the layer 123. Similarly, only the active agents contained in the matrix 124 can diffuse into the layer 125. With the FIG. 9 arrangement, the user can select whether to apply the agent or ingredient associated with matrix 121 or to apply the agent or ingredient associated with the matrix 124. Alternately, the user can sequentially apply the agent or ingredient associated with one matrix followed by application of the agent or ingredient associated with the other matrix.

FIG. 10 shows a composite structure that includes two matrices 131 and 132 that are stuck together and sandwiched between two layers 133 and 134. One of the layers 133 or 134 can be impermeable to the liquid used. By way of example, the matrices 131 and 132 can contain different active agents, including agents that are unsuitable for being packaged together (i.e., with the agents mixed together or contacting each other), such that the agents do not become mixed or contact each other until use is desired.

In order to make the structure shown in FIG. 10, it is possible as shown in FIG. 11 to start from support layers 133 and 134 having the matrices 131 and 132 coated thereon in conventional coating stations E. The matrices can contain solvents in order to facilitate the coating operation. The solvents can be volatile and eliminated from the final composite structure by heating, for example. The support layers 133 and 134 coated in this way in their respective adhesive matrices are then stuck together to form the composite structure shown in FIG. 10. Where only one matrix is to be utilized, an arrangement similar to that of FIG. 10 can be used, however, with the matrix applied using only one of the coating stations and the other substrate then superposed onto the matrix.

FIG. 12 shows a portion of the FIG. 1 glove in section so as to reveal its structure. The glove 10 includes two sheets 11 of composite structures that are assembled together along a peripheral assembly line 12 represented by dashed lines in FIG. 1. As used herein, a glove can have various forms or shapes including a mitten-shape as shown, a mitt in which no separate thumb pocket is provided, or a glove in which one or more additional separate pockets are provided for receiving fingers. Assembly of the sheets about the periphery of the glove can be performed by heat-sealing, for example, or other suitable expedients such as adhesive bonding or stitching.

Each sheet 11 is formed by superposing three layers, an outer layer 13, a matrix 14, and an inner layer 15. The matrix 14 adheres to the layers 13 and 15. The inner layer 15 in the example described is constituted by an impermeable film, thereby enabling the user's hand to be isolated from the matrix 14 in use. The outer layer 13 is constituted, in the illustrated embodiment as an example, by a hydrophilic non-woven fabric that is permeable to a liquid such as water or a water-alcohol solution, thereby enabling the user to put this liquid into contact with the matrix 14. The matrix contains an artificial tanning agent and it is arranged to release this agent when it is brought into contact with the liquid. The composition of the matrix when it is in the solvent phase can be as follows by way of example (percentages by weight): 6% polyacrylate; 15% Orgasol®; 5% DHA; 15% glycerin; 2% DHEA, acrylic adhesive in solution in ethyl acetate (40% dry extract) qsp 100%. The inner layer 15 is made of a material suitable for enabling the two sheets 11 to be assembled together by heat-sealing, e.g. a film of polyethylene (PE).

An applicator device of the invention can easily sold without requiring individual leakproof and opaque packaging, e.g., the articles can be sold in a cardboard box. At the moment of application, it is impregnated with an appropriate liquid, e.g., water, so as to put the matrix into contact with the liquid and cause the artificial tanning agent to be released. The articles can be packaged in a kit which also contains the liquid that is used to release the artificial tanning agent, with the liquid provided in one or more suitable receptacles such as bottles or packets. As noted earlier, if desired, the liquid can also include one or more skin active ingredients. Alternately, the articles can be packaged without a source of liquid so that the user uses, e.g., tap water to release the tanning agent. Thereafter, the applicator device can be moved over the skin in such a manner as to enable the artificial tanning agent released by the matrix to act on the skin.

The matrix can have elements for facilitating release of the artificial tanning agent and of the other active agent(s) contained in the matrix. These elements are constituted, for example, by water-absorbing particles or other fillers, e.g., particles of PE or of Rilsan® and they encourage the matrix to burst by creating gaps that make it easier for the liquid to pass through and for the matrix to pass through the pores or the perforations in the permeable layer. As a result the matrix can confer adhesive properties to at least one surface of the composite structure while in use. These adhesive properties can be used, for example, to hold the structure to the skin so as to decorate the skin, particularly when the structure presents a specific outline, e.g., a crescent shape as shown in FIG. 13.

The structure can also have zones of preferred passage between the skin and the matrix, for example by using a web 112 provided with openings 113 corresponding to motifs that are to be implemented as shown in FIGS. 14 and 15. The web 112 can be impermeable or hydrophobic except in the openings 113. In a variant, the web 112 is absent and the permeable layer 103 can receive a treatment, e.g., a selective silkscreen printing, so as to close the pores in the permeable layer around the motif to be implemented, or on the contrary so as to encourage diffusion of the artificial tanning agent towards the skin in said motif.

The invention makes it possible to avoid using preservatives since these are no longer required given that the artificial tanning agent can be contained in a matrix that is substantially anhydrous.

In addition, particularly when the applicator device has an impermeable layer between the matrix and the face of the device held by the fingers of the user, it can serve to avoid discoloring of the fingers.

The artificial tanning agent is relatively well protected in the matrix from external UV radiation, thus avoiding any need to keep it in an opaque bag.

The artificial tanning agent can be applied without any fear of applying excess agent since it is released relatively progressively from the matrix.

Obviously, numerous modifications and variations of the present invention are possible in light of the above teachings. It is therefore to be understood that, within the scope of the appended claims, the invention may be practiced otherwise than as specifically described herein.

What is claimed is:

1. An article for applying an artificial tanning agent to the skin, comprising:
    a first layer;
    a second layer;
    an adhesive matrix disposed between said first layer and said second layer, said adhesive matrix including an adhesive and at least one artificial tanning agent that can be applied to the skin when the adhesive matrix is contacted with a liquid, and wherein said first layer and said second layer are permanently bonded to said adhesive matrix.

2. An article as recited in claim 1, wherein the adhesive matrix includes at least one compound that is soluble in said liquid.

3. An article as recited in claim 1, wherein the adhesive matrix includes a filler comprising at least one compound capable of swelling when contacted by said liquid.

4. An article as recited in claim 1, wherein the adhesive matrix includes a filler, said filler comprising at least one compound that is substantially inert.

5. An article as recited in claim 1, wherein said liquid is one of: (a) water, and (b) a solution of water and an alcohol.

6. An article as recited in claim 1, wherein the adhesive matrix includes at least one compound for absorbing moisture.

7. An article as recited in claim 1, wherein the adhesive matrix includes 0.2% to 60% by weight of at least one moisture-absorbing compound.

8. An article as recited in claim 7, wherein the at least one moisture absorbing compound is 0.5% to 40% of the adhesive matrix.

9. An article as recited in claim 1, wherein the adhesive matrix includes at least one moisture-absorbing compound selected from the group consisting of: polyacrylates; silica; cotton fibers; starches; alginates; calcium carbonates; magnesium carbonates; viscose; cellulose; and lyophilisates.

10. An article as recited in claim 1, wherein the adhesive matrix includes at least one active agent selected from the group consisting of: vitamin C; vitamin A; vitamin F; glycerin; laponite; wetting agents; collagen; salicylic acid; do acid; caffeine; essential aromatic oils; coloring agents; anti-oxidants; free radical scavengers; moisturizers; depigmenting agents; liporegulators; antiacne agents; antidandruff agents; anti-aging agents; softeners; antiwrinkle agents; keratolitic agents; antiinflammatory agents; fresheners; healing agents; vascular protectors; antibacterial agents; antifungal agents; antiperspirants; deodorants; skin conditioners; anesthetics; immunomodulators; nourishing agents; DHEA; and melatonin.

11. An article as recited in claim 1, wherein the adhesive matrix includes at least one of magnetizable and magnetized particles.

12. An article as recited in claim 1, wherein the adhesive matrix includes an adhesive that is not soluble in water and that is in a cross-linked state.

13. An article as recited in claim 1, wherein the adhesive matrix includes at least one adhesive selected from the group consisting of: vinyl-based adhesives; PVA-based adhesives; PVP-based adhesives; pseudo-latex-based adhesives; acrylic polymer based adhesives; polyurethane-based adhesives; and latex elastomer-based adhesives.

14. An article as recited in claim 1, wherein the artificial tanning agent includes at least one of a: self tanning agent; a tanning accelerator; DHA; erythrulose; and a melanin precursor.

15. An article as recited in claim 1, wherein the artificial tanning agent is tinted.

16. An article as recited in claim 1, wherein the first layer includes a substrate selected from the group consisting of: a non-woven fabric; a foam; a woven fabric; a plastic film; and a metallized film.

17. An article as recited in claim 16, wherein said first layer includes an aerated non-woven fabric.

18. An article as recited in claim 16, wherein said first layer includes a perforated non-woven fabric.

19. An article as recited in claim 16, wherein said first layer includes one of a plastic film and a metallized film.

20. An article as recited in claim 19, wherein said first layer is perforated.

21. An article as recited in claim 1, wherein the first layer is permeable to said liquid, and said second layer is impermeable to said liquid.

22. An article as recited in claim 1, wherein the first and second layers are permeable to said liquid.

23. An article as recited in claim 1, wherein the first layer includes a hydrophilic layer and said second layer includes a hydrophobic layer.

24. An article as recited in claim 1, wherein the first and second layers are hydrophilic layers.

25. An article as recited in claim 1, wherein at least one of said first and second layers is a non-woven including hydrophilic fibers.

26. An article as recited in claim 1, wherein said first layer includes a hydrophilic layer and said second layer is impermeable to said liquid.

27. An article as recited in claim 26, wherein the first layer includes a hydrophilic non-woven fabric and wherein said second layer includes an impermeable plastic film.

28. An article as recited in claim 1, wherein the first layer is one of a woven fabric and a non-woven fabric that is hydrophilic, and the second layer is one of a woven fabric and a non-woven fabric that is hydrophobic.

29. An article as recited in claim 1, wherein the first layer is a perforated plastic film and the second layer is a hydrophilic non-woven fabric.

30. An article as recited in claim 1, wherein the first layer is a leakproof plastic film and the second layer is a hydrophilic non-woven fabric, and wherein the leakproof plastic film is at least partially covered with one of a non-woven fabric and a flocking.

31. An article as recited in claim 1, wherein at least one of said first and second layers is a perforated aerated non-woven fabric.

32. An article as recited in claim 1, wherein the article is in the form of a disk.

33. An article as recited in claim 1, wherein the article is in the form of a glove.

34. An article as recited in claim 33, wherein the glove has a layer that is impermeable to said liquid, wherein said layer that is impermeable to said liquid is disposed between the matrix and an interior of the glove.

35. An article as recited in claim 1, wherein said article is in the form of a cloth article.

36. An article as recited in claim 1, wherein the article is in the form of a roll.

37. An article as recited in claim 36, wherein the article comprises cutouts.

38. An article as recited in claim 1, wherein the first and second layers each include an outer surface, and each includes an inner surface that faces toward the matrix, and wherein the outer surface of each of said first and second layers is free from any artificial tanning agent until the adhesive matrix is contacted by said liquid.

39. An article as recited in claim 1, wherein said first and second layers provide a UV radiation barrier for said adhesive matrix.

40. An article as recited in claim 1, wherein the article includes a motif to be marked on the skin.

41. An article as recited in claim 1, wherein a surface of the article has a selective permeability for the artificial tanning agent so as to decorate the skin according to a design defined by said selective permeability.

42. A kit comprising an article as recited in claim 1, and further including a receptacle containing said liquid.

43. An article as recited in claim 1, wherein said matrix at least partially degrades when contacted by said liquid, wherein said first layer is permeable to said liquid, and wherein said second layer is impermeable to said liquid.

44. An article as recited in claim 1, wherein at least a portion of said adhesive matrix dissolves upon contact with said liquid to release the at least one artificial tanning agent, and further wherein at least one of said first and second layers is permeable to the at least one artificial tanning agent after being released by said liquid.

45. An article as recited in claim 44, wherein the at least one artificial tanning agent is dissolved by said liquid.

46. An article as recited in claim 44, wherein the adhesive matrix includes a material other than the artificial tanning agent which is dissolved by said liquid.

47. An article as recited in claim 1, wherein at least a portion of the adhesive matrix breaks apart after being contacted by said liquid to enhance contact of said artificial tanning agent with said liquid, and wherein at least one of said first and second layers is permeable to said artificial tanning agent after the adhesive matrix is contacted by said liquid.

48. An article as recited in claim 47, wherein the adhesive matrix includes a liquid-absorbing compound which swells to cause at least a portion of the adhesive matrix to break apart upon contact with said liquid.

49. An article as recited in claim 47, wherein said adhesive matrix includes a material that is soluble in said liquid to cause said at least a portion of the adhesive matrix to break apart after being contacted by said liquid.

50. A method for making an article for applying an artificial tanning agent to the skin comprising:

incorporating an artificial tanning agent into an adhesive-based matrix; and disposing the adhesive-based matrix between a first layer and a second layer, wherein at least one of said first layer and said second layer is permeable to a liquid such that said artificial tanning agent can be applied to the skin when the adhesive-based matrix is contacted with said liquid.

51. A method as recited in claim 50, wherein the adhesive-based matrix does not impregnate at least one of said first and second layers to more than 25% of its thickness.

52. A method as recited in claim 50, wherein the adhesive-based matrix does not pass through an aqueous phase during manufacture.

53. A method as recited in claim 50, wherein the at least one of said first and second layers which is permeable to allow the artificial tanning agent to be applied to the skin is fixed to the adhesive-based matrix by adhesive contact.

54. A method as recited in claim 50, wherein the article formed with the adhesive-based matrix and the first and second layers includes at least one cut out portion in the form of a motif to be marked on the skin.

55. A method as recited in claim 50, wherein the article formed with the adhesive-based matrix and the first and second layers is covered by a web that is impermeable to the artificial tanning agent, and wherein said web includes perforations arranged to enable at least one motif to be marked on the skin.

56. A method as recited in claim 50, wherein a surface of the article is treated in selective manner so as to allow the article to selectively mark the skin to decorate the skin.

57. A method as recited in claim 50, further including providing in said adhesive-based matrix a material that causes said adhesive-based matrix to at least one of: (a) partially dissolve after being contacted by said liquid, and (b) at least partially break apart after being contacted by said liquid;

wherein the artificial tanning agent is released after the adhesive-based matrix is contacted by said liquid.

58. An article for applying a skin care product, comprising:

a first layer;

a second layer;

an adhesive matrix disposed between said first substrate layer and said second substrate layer, said adhesive matrix including an artificial tanning agent, and wherein upon contact with a liquid to apply the artificial tanning agent, the adhesive matrix at least partially degrades to release said artificial tanning agent, and wherein said first substrate layer is permeable to said liquid such that said artificial tanning agent can be applied to the skin when said article is wetted with said liquid, and wherein said second layer is impermeable to said liquid, and further wherein said artificial tanning agent is soluble in said liquid.

59. An article as recited in claim 58, wherein said liquid includes water.

60. An article as recited in claim 59, wherein said liquid further includes an alcohol.

61. An article as recited in claim 60, further including a receptacle for holding said liquid.

62. An article as recited in claim 58, wherein said first and second layers are UV radiation barriers.

63. An article as recited in claim 58, wherein said second layer includes at least one of a plastic film and a metalized film.

64. An article as recited in claim 63, wherein said first layer is an aerated non-woven having apertures therein.

65. An article as recited in claim 58, wherein said second layer includes a ply that is impermeable to said liquid, said second layer further including at least one of a flocking and a fabric at least partially covering said ply.

66. An article as recited in claim 58, wherein said adhesive matrix includes a liquid-absorbing compound which swells to cause at least a portion of the adhesive matrix to break apart upon contact with said liquid.

67. An article as recited in claim 58, wherein said adhesive matrix includes a composition other than said artificial tanning agent which is soluble in said liquid to degrade said matrix.

68. An article as recited in claim 58, wherein said artificial tanning agent is anhydrous prior to application of said liquid.

* * * * *